United States Patent
Hedrick et al.

(10) Patent No.: US 7,157,244 B2
(45) Date of Patent: Jan. 2, 2007

(54) ADENOSINE RECEPTOR

(75) Inventors: Joseph A. Hedrick, South River, NJ (US); Jean E. Lachowicz, Berkeley Heights, NJ (US); Wei Wang, Palo Alto, CA (US); Eric L. Gustafson, Annandale, NJ (US)

(73) Assignee: Schering Corporation, Kenilworth, NJ (US)

( * ) Notice: Subject to any disclaimer, the term of this patent is extended or adjusted under 35 U.S.C. 154(b) by 1070 days.

(21) Appl. No.: 09/765,034

(22) Filed: Jan. 17, 2001

(65) Prior Publication Data

US 2002/0137887 A1    Sep. 26, 2002

(51) Int. Cl.
*C12P 21/06* (2006.01)
*C12N 5/00* (2006.01)
*C12N 15/00* (2006.01)
*C07H 21/04* (2006.01)
*C07K 14/00* (2006.01)

(52) U.S. Cl. .................. 435/69.1; 435/325; 435/252.3; 435/348; 435/349; 435/361; 435/365; 435/353; 435/367; 435/252.33; 435/253.3; 435/252.5; 435/320.1; 536/23.5; 530/350

(58) Field of Classification Search ................ 536/23.5; 530/350, 412; 435/69.1, 325, 252.3, 348, 435/349, 361, 365, 353, 367, 252.33, 253.3, 435/252.5, 320.1

See application file for complete search history.

(56) References Cited

U.S. PATENT DOCUMENTS 5,871,963 A * 2/1999 Conley et al. ............. 435/69.1

FOREIGN PATENT DOCUMENTS

| WO | WO 97/20045 | * | 6/1997 |
| WO | WO 00/22131 | * | 4/2000 |

OTHER PUBLICATIONS

Kaiser, Sonya M. and Quinn, Ronald J., Adenosine receptors as potential therapeutic targets. *Drug Discovery Today* 4(12), 542-551 (1999).
Muller, C.E., Adenosine Receptor Ligands-Recent Developments Part I. Agonists. *Current Medicinal Chemistry* 7:1269-1288 (2000).
Poulsen, Sally-Ann and Quinn, Ronald J., Adenosine Receptors: New Opportunities for Future Drugs. *Bioorganic & Medicinal Chemistry* 6:619-641 (1998).

* cited by examiner

*Primary Examiner*—Lorraine Spector
*Assistant Examiner*—Dong Jiang
(74) *Attorney, Agent, or Firm*—Grant E. Reed

(57) ABSTRACT

The present invention provides an isolated mammalian adenosine receptor, isolated or recombinant nucleic acids and recombinant vectors encoding the same, host cells comprising the nucleic acids and vectors, and methods of making the receptor using the host cells. This invention further provides antibodies and antigen binding fragments thereof which specifically bind to the receptor and are useful for treating medical conditions caused or mediated by adenosine. Also provided are screening methods for identifying specific agonists and antagonists of the mammalian adenosine receptor.

28 Claims, No Drawings

SEQUENCE LISTING

<160> NUMBER OF SEQ ID NOS: 4

<210> SEQ ID NO 1
<211> LENGTH: 1338
<212> TYPE: DNA
<213> ORGANISM: homo sapiens
<220> FEATURE:
<221> NAME/KEY: CDS
<222> LOCATION: (1)..(1005)

<400> SEQUENCE: 1

```
atg ctg ggg atc atg gca tgg aat gca act tgc aaa aac tgg ctg gca     48
Met Leu Gly Ile Met Ala Trp Asn Ala Thr Cys Lys Asn Trp Leu Ala
```

-continued

| | | | |
|---|---|---|---|
| gca gag gct gcc ctg gaa aag tac tac ctt tcc att ttt tat ggg att | | | 96 |
| Ala Glu Ala Ala Leu Glu Lys Tyr Tyr Leu Ser Ile Phe Tyr Gly Ile | | | |
| 20 25 30 | | | |
| gag ttc gtt gtg gga gtc ctt gga aat acc att gtt gtt tac ggc tac | | | 144 |
| Glu Phe Val Val Gly Val Leu Gly Asn Thr Ile Val Val Tyr Gly Tyr | | | |
| 35 40 45 | | | |
| atc ttc tct ctg aag aac tgg aac agc agt aat att tat ctc ttt aac | | | 192 |
| Ile Phe Ser Leu Lys Asn Trp Asn Ser Ser Asn Ile Tyr Leu Phe Asn | | | |
| 50 55 60 | | | |
| ctc tct gtc tct gac tta gct ttt ctg tgc acc ctc ccc atg ctg ata | | | 240 |
| Leu Ser Val Ser Asp Leu Ala Phe Leu Cys Thr Leu Pro Met Leu Ile | | | |
| 65 70 75 80 | | | |
| agg agt tat gcc aat gga aac tgg ata tat gga gac gtg ctc tgc ata | | | 288 |
| Arg Ser Tyr Ala Asn Gly Asn Trp Ile Tyr Gly Asp Val Leu Cys Ile | | | |
| 85 90 95 | | | |
| agc aac cga tat gtg ctt cat gcc aac ctc tat acc agc att ctc ttt | | | 336 |
| Ser Asn Arg Tyr Val Leu His Ala Asn Leu Tyr Thr Ser Ile Leu Phe | | | |
| 100 105 110 | | | |
| ctc act ttt atc agc ata gat cga tac ttg ata att aag tat cct ttc | | | 384 |
| Leu Thr Phe Ile Ser Ile Asp Arg Tyr Leu Ile Ile Lys Tyr Pro Phe | | | |
| 115 120 125 | | | |
| cga gaa cac ctt ctg caa aag aaa gag ttt gct att tta atc tcc ttg | | | 432 |
| Arg Glu His Leu Leu Gln Lys Lys Glu Phe Ala Ile Leu Ile Ser Leu | | | |
| 130 135 140 | | | |
| gcc att tgg gtt tta gta acc tta gag tta cta ccc ata ctt ccc ctt | | | 480 |
| Ala Ile Trp Val Leu Val Thr Leu Glu Leu Leu Pro Ile Leu Pro Leu | | | |
| 145 150 155 160 | | | |
| ata aat cct gtt ata act gac aat ggc acc acc tgt aat gat ttt gca | | | 528 |
| Ile Asn Pro Val Ile Thr Asp Asn Gly Thr Thr Cys Asn Asp Phe Ala | | | |
| 165 170 175 | | | |
| agt tct gga gac ccc aac tac aac ctc att tac agc atg tgt cta aca | | | 576 |
| Ser Ser Gly Asp Pro Asn Tyr Asn Leu Ile Tyr Ser Met Cys Leu Thr | | | |
| 180 185 190 | | | |
| ctg ttg ggg ttc ctt att cct ctt ttt gtg atg tgt ttc ttt tat tac | | | 624 |
| Leu Leu Gly Phe Leu Ile Pro Leu Phe Val Met Cys Phe Phe Tyr Tyr | | | |
| 195 200 205 | | | |
| aag att gct ctc ttc cta aag cag agg aat agg cag gtt gct act gct | | | 672 |
| Lys Ile Ala Leu Phe Leu Lys Gln Arg Asn Arg Gln Val Ala Thr Ala | | | |
| 210 215 220 | | | |
| ctg ccc ctt gaa aag cct ctc aac ttg gtc atc atg gca gtg gta atc | | | 720 |
| Leu Pro Leu Glu Lys Pro Leu Asn Leu Val Ile Met Ala Val Val Ile | | | |
| 225 230 235 240 | | | |
| ttc tct gtg cct ttt aca ccc tat cac gtc atg cgg aat gtg agg atc | | | 768 |
| Phe Ser Val Pro Phe Thr Pro Tyr His Val Met Arg Asn Val Arg Ile | | | |
| 245 250 255 | | | |
| gct tca cgc ctg ggg agt tgg aag cag tat cag tgc act cag gtc gtc | | | 816 |
| Ala Ser Arg Leu Gly Ser Trp Lys Gln Tyr Gln Cys Thr Gln Val Val | | | |
| 260 265 270 | | | |
| atc aac tcc ttt tac att gtg aca cgg cct ttg gcc ttt ctg aac agt | | | 864 |
| Ile Asn Ser Phe Tyr Ile Val Thr Arg Pro Leu Ala Phe Leu Asn Ser | | | |
| 275 280 285 | | | |
| gtc atc aac cct gtc ttc tat ttt ctt ttg gga gat cac ttc agg gac | | | 912 |
| Val Ile Asn Pro Val Phe Tyr Phe Leu Leu Gly Asp His Phe Arg Asp | | | |
| 290 295 300 | | | |
| atg ctg atg aat caa ctg aga cac aac ttc aaa tcc ctt aca tcc ttt | | | 960 |
| Met Leu Met Asn Gln Leu Arg His Asn Phe Lys Ser Leu Thr Ser Phe | | | |
| 305 310 315 320 | | | |
| agc aga tgg gct cat gaa ctc cta ctt tca ttc aga gaa aag tga | | | 1005 |

```
Ser Arg Trp Ala His Glu Leu Leu Ser Phe Arg Glu Lys
            325                 330                 335 ggggcttgtg aaacagattg ttctacagat gaatctgtaa gccagttaca gtttgcctta    1065
actcatagac atcaatcaga gagtgtcaca gatttaacct tgatctaaag acaagttgta    1125
cccagagtat gtgaaaagaa tgggacgaca agaatgtact ggtttcttcc tctaagaatt    1185
gaaaggagtt gaactgcctt atgtttgggc atgtaactcc aaaatactag gtagtataag    1245
gctttctcaa tcagtgcaaa aatggaagat atataaagca acaagttgtc tgcatttgat    1305
cactggtcag attgtaaaaa aaaaaaaaaa aaa                                 1338
```

<210> SEQ ID NO 2
<211> LENGTH: 334
<212> TYPE: PRT
<213> ORGANISM: homo sapiens

<400> SEQUENCE: 2

```
Met Leu Gly Ile Met Ala Trp Asn Ala Thr Cys Lys Asn Trp Leu Ala
 1               5                  10                  15

Ala Glu Ala Ala Leu Glu Lys Tyr Tyr Leu Ser Ile Phe Tyr Gly Ile
            20                  25                  30

Glu Phe Val Val Gly Val Leu Gly Asn Thr Ile Val Tyr Gly Tyr
        35                  40                  45

Ile Phe Ser Leu Lys Asn Trp Asn Ser Ser Asn Ile Tyr Leu Phe Asn
    50                  55                  60

Leu Ser Val Ser Asp Leu Ala Phe Leu Cys Thr Leu Pro Met Leu Ile
65                  70                  75                  80

Arg Ser Tyr Ala Asn Gly Asn Trp Ile Tyr Gly Asp Val Leu Cys Ile
                85                  90                  95

Ser Asn Arg Tyr Val Leu His Ala Asn Leu Tyr Thr Ser Ile Leu Phe
            100                 105                 110

Leu Thr Phe Ile Ser Ile Asp Arg Tyr Leu Ile Ile Lys Tyr Pro Phe
        115                 120                 125

Arg Glu His Leu Leu Gln Lys Lys Glu Phe Ala Ile Leu Ile Ser Leu
    130                 135                 140

Ala Ile Trp Val Leu Val Thr Leu Glu Leu Leu Pro Ile Leu Pro Leu
145                 150                 155                 160

Ile Asn Pro Val Ile Thr Asp Asn Gly Thr Thr Cys Asn Asp Phe Ala
                165                 170                 175

Ser Ser Gly Asp Pro Asn Tyr Asn Leu Ile Tyr Ser Met Cys Leu Thr
            180                 185                 190

Leu Leu Gly Phe Leu Ile Pro Leu Phe Val Met Cys Phe Phe Tyr Tyr
        195                 200                 205

Lys Ile Ala Leu Phe Leu Lys Gln Arg Asn Arg Gln Val Ala Thr Ala
    210                 215                 220

Leu Pro Leu Glu Lys Pro Leu Asn Leu Val Ile Met Ala Val Val Ile
225                 230                 235                 240

Phe Ser Val Pro Phe Thr Pro Tyr His Val Met Arg Asn Val Arg Ile
                245                 250                 255

Ala Ser Arg Leu Gly Ser Trp Lys Gln Tyr Gln Cys Thr Gln Val Val
            260                 265                 270

Ile Asn Ser Phe Tyr Ile Val Thr Arg Pro Leu Ala Phe Leu Asn Ser
        275                 280                 285

Val Ile Asn Pro Val Phe Tyr Phe Leu Leu Gly Asp His Phe Arg Asp
    290                 295                 300
```

```
Met Leu Met Asn Gln Leu Arg His Asn Phe Lys Ser Leu Thr Ser Phe
305                 310                 315                 320

Ser Arg Trp Ala His Glu Leu Leu Leu Ser Phe Arg Glu Lys
                325                 330

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: sense PCR
      primer

<400> SEQUENCE: 3
cggaattcat gctggggatc atggcatgga atgcaac                              37

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: antisense
      PCR primer

<400> SEQUENCE: 4
tatgcggccg cccaccacac tggactagtg gatcctca                             38
```

ADENOSINE RECEPTOR

TECHNICAL FIELD

The present invention relates to mammalian adenosine receptors. More particularly, it relates to human adenosine receptors, isolated nucleic acids and recombinant vectors encoding the receptors, to methods of making the receptors, to methods of making fragments or fusion proteins of the receptors using recombinant DNA methodology or chemical synthesis, and to methods of using the receptors in screening systems to identify agonists and antagonists of the receptors useful for the treatment of various diseases.

BACKGROUND OF THE INVENTION

Adenosine is a purine nucleotide that has been demonstrated to produce a number of physiological functions. In the cardiovascular system, adenosine causes vasodilation, hypotension, and reversal of tachycardia. Adenosine is currently used to treat ventricular arrhythmia. Adenosine is released during hypoxia and has been shown to protect the myocardium by increasing energy supply and reducing energy demand. In cardiac myocytes and other cell types, adenosine is released in large amounts during the reperfusion phase following ischemia. Reperfusion injury due to oxygen radicals is a major factor in infarct severity. Adenosine has been shown to reduce infarct size following ischemia-reperfusion in cardiac myocytes, indicating potential value in cellular protection. In the kidney, adenosine affects outer medullary blood flow, inner medullary blood flow, renin secretion, urine flow, and sodium excretion. Blockade of adenosine receptors in the kidney may be therapeutically useful in chronic renal disease. In the brain, adenosine attenuates neuronal degeneration of cells deprived of oxygen or glucose. This effect is mimicked by the non-selective adenosine agonist 5'-N-Ethyl-carboxamido-adenosine (NECA). In the striatum and hippocampus, adenosine antagonists have been shown to increase acetylcholine release, an effect therapeutically relevant to neurodegenerative diseases such as Alzheimer's Disease and Parkinson's Disease. In inflammatory conditions such as asthma, adenosine has been shown to stimulate bronchonstriction and to cause mast cell degranulation. Thus, adenosine receptor antagonists may have therapeutic utility in these situations. Adenosine has also been shown to down-regulate monocyte/macrophage pro-inflammatory functions. Accordingly, in certain types of inflammatory conditions, an adenosine receptor agonist may have therapeutic utility.

In view of the important role that adenosines play in many physiological processes and medical conditions, there is a need for materials and methods useful for the identification of agonists and antagonists selective for the specific types of adenosine receptors.

SUMMARY OF THE INVENTION

The present invention fills the foregoing need by providing such materials and methods. More particularly, this invention provides a novel mammalian adenosine receptor, isolated nucleic acids or recombinant nucleic acids encoding the receptor, and recombinant vectors and host cells comprising such nucleic acids. The adenosine receptor can be actively expressed in mammalian cells where it displays active ligand binding and positive intracellular signaling upon ligand activation. This novel receptor has high affinity for adenosine. This invention further provides methods for the discovery of selective agonists and antagonists of the receptor that may be useful in the treatment and management of a variety of diseases.

This invention provides an isolated polypeptide comprising a sequence defined by SEQ ID NO: 2 or a subsequence thereof.

This invention also provides polypeptides comprising a fragment of a polypeptide having an amino acid sequence corresponding to the sequence of at least about 8 contiguous residues of the amino acid sequence of SEQ ID NO: 2. Preferably, the polypeptides comprise at least about 12, more preferably at least about 20, and most preferably at least about 30 such residues.

Still further, this invention provides fusion proteins comprising a polypeptide defined by SEQ ID NO: 2 or a fragment therefrom covalently linked to a fusion partner.

The present invention also provides isolated or recombinant nucleic acids selected from the group consisting of:

(a) A nucleic acid encoding a polypeptide comprising an amino acid sequence defined by SEQ ID NO: 2 or a subsequence thereof;

(b) A nucleic acid that hybridizes under moderately stringent conditions to the nucleic acid of (a) and encodes a polypeptide that (i) binds adenosine and (ii) is at least 80% identical to a receptor encoded by the nucleic acid of (a); and (c) A nucleic acid that, due to the degeneracy of the genetic code, encodes a mammalian adenosine receptor encoded by a nucleic acid of (a) or (b).

This invention further provides methods of making a polypeptide comprising culturing a host cell comprising a nucleic acid encoding a mammalian adenosine receptor comprising an amino acid sequence defined by SEQ ID NO: 2 or a subsequence thereof, under conditions in which the nucleic acid is expressed. In some embodiments, the method further comprises isolation of the polypeptide from the culture.

This invention also provides a recombinant nucleic acid comprising a sequence having at least about 70% identity over a stretch of at least about 30 nucleotides to the nucleic acid sequence of SEQ ID NO: 1, useful, e.g., as a probe or PCR primer for a related gene. Another embodiment further includes a polypeptide comprising at least about 60% identity over a stretch of at least about 20 amino acids to the amino acid sequence of SEQ ID NO: 2.

The present invention also provides antibodies, both polyclonal and monoclonal, that specifically bind to one or more of the adenosine receptors or to polypeptides therefrom, and anti-idiotypic antibodies, both monoclonal and polyclonal, which specifically bind to the foregoing antibodies.

This invention further provides a method for producing a mammalian adenosine receptor comprising culturing a host cell comprising a nucleic acid encoding a mammalian adenosine receptor comprising an amino acid sequence defined by SEQ ID NO: 2 or a subsequence thereof, under conditions in which the nucleic acid is expressed. In one embodiment the receptor is isolated from the culture.

The present invention also provides a method for identifying an adenosine agonist or antagonist comprising:

(a) Contacting a polypeptide having an amino acid sequence defined by SEQ ID NO: 2 or a subsequence thereof, in the presence of a known amount of labeled adenosine or a surrogate thereof with a sample to be tested for the presence of an adenosine agonist or antagonist; and (b) Measuring the amount of labeled adenosine or surrogate specifically bound to the receptor;

whereby an adenosine agonist or antagonist in the sample is identified by measuring substantially reduced binding of the labeled adenosine or surrogate to the adenosine receptor, compared to what would be measured in the absence of such agonist or antagonist.

In a preferred embodiment, membranes isolated from mammalian cells comprising a nucleic acid encoding the adenosine receptor are used as the source of the receptor.

The present invention also provides a method for identifying an agonist or antagonist of a mammalian adenosine receptor comprising:

(a) contacting cells expressing a polypeptide comprising an amino acid sequence defined by SEQ ID NO: 2 or a subsequence thereof, in the presence of a known amount of adenosine or surrogate thereof with a sample to be tested for the presence of a mammalian adenosine agonist or antagonist; and (b) measuring at least one cellular function modulated by the binding of a ligand to said receptor present in the cells;

whereby a mammalian adenosine receptor agonist or antagonist in the sample is identified by measuring its effect on said cellular function compared to what would be measured in the absence of such agonist or antagonist.

Examples of cellular functions modulated by the binding of a ligand to a mammalian adenosine receptor include: intracellular second messenger pathways activated via the adenosine receptors (e.g., cyclic AMP, calcium, inositol phosphate and MAP kinase), changes in cell growth rate, secretion of hormones, receptor-stimulated $Ca^{2++}$ mobilization, mitogenic effects etc., This invention still further provides a method for treating adenosine-mediated medical conditions comprising administering to a mammal afflicted with a medical condition caused or mediated by adenosine, an effective amount of an agonist or antagonist of the adenosine receptor that specifically binds to a mammalian adenosine receptor having an amino acid sequence defined by SEQ ID NO: 2, or a subsequence thereof, and pharmaceutical compositions comprising one or more of such agonist or antagonist and a pharmaceutically acceptable carrier. Preferably, the mammal is a human being.

This invention also provides a method for measuring expression of a mammalian adenosine receptor gene in a biological sample comprising the steps of:

(a) isolating messenger RNA from the sample;
(b) reverse transcribing the messenger RNA into cDNA;
(c) performing PCR on the cDNA using oligonucleotide primers derived from a nucleic acid defined by SEQ ID NO: 1; and
(d) quantifying the amount of PCR product.

DESCRIPTION OF THE INVENTION

All references cited herein are hereby incorporated herein in their entirety by reference.

Adenosine Receptor Characterization

The nucleotide sequence of the complete open reading frame and the corresponding amino acid sequence of the human adenosine receptor of this invention are defined in SEQ ID NO: 1 and SEQ ID NO: 2, respectively. The cloned receptor resembles a member of the G-protein coupled receptor super-family that contains 7-transmembrane domains. The cloned receptor is able to bind ligands, for example, adenosine, as demonstrated with radioligand saturation and competition assays. Adenosine is also capable of activating the cloned receptor resulting in intracellular responses, as shown by measurement of intracellular $Ca^{2+}$ flux.

As used herein, the term "ligand" is defined to mean any molecule capable of specifically binding to the mammalian adenosine receptors of the invention. Thus, adenosine itself is a ligand, as are agonists and antagonists that may compete with adenosine for specific binding to the receptors.

The modifications that occur in a polypeptide often will be a function of how it is made. For polypeptides made by expressing a cloned gene in a host, for instance, the nature and extent of the modifications in large part will be determined by the host cell's post-translational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylating host, generally a eukaryotic cell. Insect cells often carry out the same post-translational glycosylations as mammalian cells do and, for this reason, insect cell expression systems have been developed to express efficiently mammalian proteins having the native patterns of glycosylation, inter alia. Similar considerations apply to other modifications.

It will be appreciated that the same type of modification may be present in the same or varying degrees at several sites in a given polypeptide. Also, a given polypeptide may contain many types of modifications.

The term "polypeptide" encompasses all such modifications, particularly those that are present in polypeptides synthesized by expressing a polynucleotide in a host cell.

"Variant(s)", as the term is used herein, are polynucleotides or polypeptides that differ from a reference polynucleotide or polypeptide respectively. Variants in this sense are described below and elsewhere in the present disclosure in greater detail. (1) A polynucleotide that differs in nucleotide sequence from another, reference polynucleotide. Changes in the nucleotide sequence of the variant may be silent, i.e. they may not alter the amino acids encoded by the polynucleotide. Where alterations are limited to silent changes of this type a variant will encode a polypeptide with the same amino acid sequence as the reference polypeptide. Changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below. (2) A polypeptide that differs in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination. (3) A variant may also be a fragment of a polynucleotide or polypeptide of the invention that differs from a reference polynucleotide or polypeptide sequence by being shorter than the reference sequence, such as by a terminal or internal deletion. A variant of a polypeptide of the invention also includes a polypeptide which retains essentially the same biological function or activity as such polypeptide, e.g., pro-proteins which can be activated by cleavage of the pro-protein portion to produce an active mature polypeptide. (4) A variant may also be (i) one in which one or more of the amino acid residues are substituted with a conserved or non-conserved amino acid residue (preferably a conserved amino acid residue) and such substituted amino acid residue may or may not be encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a pro-protein sequence. (5) A variant of the polynucleotide or polypeptide may be a naturally occurring variant such as a naturally occurring allelic variant, or it may be a variant that is not known to occur naturally. Such non-naturally occurring variants or the polynucleotide may be made by mutagenesis techniques, including those applied to polynucleotides, cells or organisms, or may be made by recombinant means. Among polynucleotide variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions. All such variants defined above are deemed to be within the scope of those skilled in the art from the teachings herein and from the art.

The present invention also encompasses fragments, analogs and physical variants of the disclosed adenosine receptor. As used herein, the term "polypeptide" or "peptide" means a fragment or segment, e.g., of a mammalian adenosine receptor having an amino acid sequence defined by SEQ ID NO: 2 which comprises a subsequence of the complete amino acid sequence of the receptor containing at least about 8, preferably at least about 12, more preferably at least about 20, and most preferably at least about 30 or more contiguous amino acid residues, up to and including the total number of residues in the complete receptor.

The polypeptides of the invention can comprise any part of the complete sequence of such a receptor. Thus, although they could be produced by proteolytic cleavage of an intact receptor, they can also be made by chemical synthesis or by the application of recombinant DNA technology and are not limited to polypeptides delineated by proteolytic cleavage sites. The polypeptides, either alone or cross-linked or conjugated to a carrier molecule to render them more immunogenic, are useful as antigens to elicit the production of antibodies. The antibodies can be used, e.g., in immunoassays of the intact receptors, for immunoaffinity purification, etc.

The term "analog(s)" means a mammalian adenosine receptor of the invention which has been modified by deletion, addition, modification or substitution of one or more amino acid residues in the wild-type receptor. It encompasses allelic and polymorphic variants, and also muteins and fusion proteins which comprise all or a significant part of such a mammalian adenosine receptor, e.g., covalently linked via a side-chain group or terminal residue to a different protein, polypeptide or moiety (fusion partner).

Some amino acid substitutions are preferably "conservative", with residues replaced with physically or chemically similar residues, such as Gly/Ala, Asp/Glu, Val/Ile/Leu, Lys/Arg, Asn/Gln and Phe/Trp/Tyr. Analogs having such conservative substitutions typically retain substantial adenosine binding activity. Other analogs, which have non-conservative substitutions such as Asn/Glu, Val/Tyr and His/Glu, may substantially lack such activity. Nevertheless, such analogs are useful because they can be used as antigens to elicit production of antibodies in an immunologically competent host. Because these analogs retain many of the epitopes (antigenic determinants) of the wild-type receptors from which they are derived, many antibodies produced against them can also bind to the active-conformation or denatured wild-type receptors. Accordingly, such antibodies can also be used, e.g., for the immunopurification or immunoassay of the wild-type receptors.

Some analogs are truncated variants in which residues have been successively deleted from the amino- and/or carboxyl-termini, while substantially retaining the characteristic ligand binding activity.

Modifications of amino acid residues may include but are not limited to aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine.

Other analogs are mammalian adenosine receptors containing modifications, such as incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those that have molecular shapes similar to phosphate groups.

Analogs of the mammalian adenosine receptors can be prepared by chemical synthesis or by using site-directed mutagenesis [Gilhman et al., *Gene* 8:81 (1979); Roberts et al., *Nature*, 328:731 (1987) or Innis (Ed.), 1990, *PCR Protocols. A Guide to Methods and Applications*, Academic Press, New York, N.Y.] or the polymerase chain reaction method [PCR; Saiki et al., *Science* 239:487 (1988)], as exemplified by Daugherty et al. [*Nucleic Acids Res.* 19:2471 (1991)] to modify nucleic acids encoding the complete receptors. Adding epitope tags for purification or detection of recombinant products is envisioned.

General techniques for nucleic acid manipulation and expression that can be used to make the analogs are described generally, e.g., in Sambrook, et al., *Molecular Cloning: A Laboratory Manual* (2d ed.), 1989, Vols. 1–3, Cold Spring Harbor Laboratory. Techniques for the synthesis of polypeptides are described, for example, in Merrifield, *J. Amer. Chem. Soc.* 85:2149 (1963); Merrifield, *Science* 232:341 (1986); and Atherton et al., *Solid Phase Peptide Synthesis: A Practical Approach*, 1989, IRL Press, Oxford.

Still other analogs are prepared by the use of agents known in the art for their usefulness in cross-linking proteins through reactive side groups. Preferred derivatization sites with cross-linking agents are free amino groups, carbohydrate moieties and cysteine residues.

Substantial retention of ligand binding activity by the foregoing analogs of the mammalian adenosine receptors typically entails retention of at least about 50%, preferably at least about 75%, more preferably at least about 80%, and most preferably at least about 90% of the adenosine binding activity and/or specificity of the corresponding wild-type receptor.

Nucleic Acids and Expression Vectors

As used herein, the term "isolated nucleic acid" means a nucleic acid such as an RNA or DNA molecule, or a mixed polymer, which is substantially separated from other components that are normally found in cells or in recombinant DNA expression systems. These components include but are not limited to ribosomes, polymerases, serum components, and flanking genomic sequences. The term thus embraces a nucleic acid that has been removed from its naturally occurring environment, and includes recombinant or cloned DNA isolates and chemically synthesized analogs or analogs biologically synthesized by heterologous systems. A substantially pure molecule includes isolated forms of the molecule.

An isolated nucleic acid will generally be a homogeneous composition of molecules but may, in some embodiments, contain minor heterogeneity. Such heterogeneity is typically found at the ends of nucleic acid coding sequences or in regions not critical to a desired biological function or activity.

A "recombinant nucleic acid" is defined either by its method of production or structure. Some recombinant nucleic acids are thus made by the use of recombinant DNA techniques which involve human intervention, either in manipulation or selection. Others are made by fusing two fragments that are not naturally contiguous to each other. Engineered vectors are encompassed, as well as nucleic acids comprising sequences derived using any synthetic oligonucleotide process.

For example, a wild-type codon may be replaced with a redundant codon encoding the same amino acid residue or a conservative substitution, while at the same time introducing or removing a nucleic acid sequence recognition site. Similarly, nucleic acid segments encoding desired functions may be fused to generate a single genetic entity encoding a desired combination of functions not found together in nature. Although restriction enzyme recognition sites are often the targets of such artificial manipulations, other site-specific targets, e.g., promoters, DNA replication sites, regulation sequences, control sequences, or other useful features may be incorporated by design. Sequences encoding epitope tags for detection or purification as described above may also be incorporated.

A nucleic acid "fragment" is defined herein as a nucleotide sequence comprising at least about 17, generally at least about 25, preferably at least about 35, more preferably at least about 45, and most preferably at least about 55 or more contiguous nucleotides.

This invention further encompasses recombinant DNA molecules and fragments having sequences that are identical or highly homologous to those described herein. The nucleic acids of the invention may be operably linked to DNA segments that control transcription, translation, and DNA replication.

"Identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Similarity" between two polypeptides is determined by comparing the amino acid sequence and its conserved amino acid substitutes of one polypeptide to the sequence of a second polypeptide. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48:1073 (1988)). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12 (1):387 (1984)), BestFit, BLASTP, BLASTN, and FASTA (Altschul, S. F. et al, *J. Mol. Biol.* 215:403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol* 215:403–410 (1990). The well-known Smith Waterman algorithm may also be used to determine identity.

Preferred parameters for polypeptide sequence comparison include the following:

1) Algorithm: Needleman and Wunsch, *J. Mol. Biol* 48:443–453 (1970)

Comparison matrix: BLOSSUM62 from Hentikoff and Hentikoff, *Proc. Natl. Acad. Sci.*

USA. 89:10915–10919 (1992)

Gap Penalty: 12

Gap Length Penalty: 4

A program useful with these parameters is publicly available as the "gap" program from Genetics Computer Group, located in Madison, Wis. The aforementioned parameters are the default parameters for peptide comparisons (along with no penalty for end gaps).

Preferred parameters for polynucleotide comparison include the following:

1) Algorithm: Needleman and Wunsch, *J. Mol. Biol.* 48:443–453 (1970)

Comparison matrix: matches=+10, mismatch=0

Gap Penalty: 50

Gap Length Penalty: 3

Available as the Gap program from Genetics Computer Group, located in Madison, Wis.

Given above are the default parameters for nucleic acid comparisons.

Preferred polynucleotide embodiments further include an isolated polynucleotide comprising a polynucleotide sequence having at least a 50, 60, 70, 80, 85, 90, 95, 97 or 100% identity to the reference sequence of SEQ ID NO: 1, wherein said polynucleotide sequence may be identical to the reference sequence of SEQ ID NO: 1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO: 1 by the integer defining the percent identity divided by 100 and then subtracting that product from said total number of nucleotides in SEQ ID NO: 1, or: $n_n x_n-(x_n y)$, wherein $n_n$ is the number of nucleotide alterations, $X_n$ is the number of nucleotides in SEQ ID NO: 1, y is 0.50 for 50%, 0.60 for 60%, 0.70 for 70%, 0.80 for 80%, 0.85 for 85%, 0.90 for 90%, 0.95 for 95%, 0.97% for 0.97% or 1.00 for 100%, and is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO: 2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO: 2, that is it may be 100% identical, or it may include up to a certain integer number of amino acid alterations as compared to the reference sequence such that the percent identity is less than 100% identity. Such alterations are selected form the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of amino acids in SEQ ID NO: 2 by the integer defining the percent identity divided by 100 and then subtracting that product from said total number of amino acids in SEQ ID NO: 2, or $n_n=X_n-(X_n y)$, wherein $n_n$ is the number of amino acid alterations, $X_n$ is the total number of amino acids in SEQ ID NO: 2, y is, for instance 0.70 for 70%, 0.80 for 80%, 0.85 for 85% etc., is the symbol for the multiplication operator, and wherein any non-integer product of $X_n$ and y is rounded down to the nearest integer prior to subtracting it from $X_n$.

Preferred polypeptide embodiments further include an isolated polypeptide comprising a polypeptide having at least a 50, 60, 70, 80, 85, 90, 95, 97 or 100% identity to a polypeptide reference sequence of SEQ ID NO: 2, wherein said polypeptide sequence may be identical to the reference sequence of SEQ ID NO: 2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino-or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO: 2 by the integer defining the percent identity divided by 100 and then subtraction that product from said total number of amino acids in SEQ ID NO: 2, or: $n_a x_a-(x_a y)$, wherein $n_a$ is the number of amino acid alterations, $x_a$ is the total number of amino acids in SEQ ID NO: 2, y is 0.50 for 50%, 0.60 for 60%, 0.70 for 70%, 0.80 for 80%, 0.85 for 85%, 0.95 for 95%, 0.97 for 97% or 1.00 for 100%, and is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO: 2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino-or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO: 2 by the integer defining the percent identity divided by 100 and then subtracting that product from said total number of amino acids in SEQ ID NO: 2, or $n_a=x_a (x_a y)$, wherein $n_a$ is the number of amino acid alterations, $X_a$ is the total number of amino acids in SEQ ID NO: 2, y is, for instance 0.70 for 70%, 0.80 for 80%, 0.85 for 85% etc., and is the symbol for the multiplication operator, and wherein any non-integer product of $x_a$ and y is rounded down to the nearest integer prior to subtracting it from $x_a$.

The term "homology", as it is used herein, embraces both identity and similarity.

Some of the physical variants have substantial amino acid sequence homology with the amino acid sequences of the mammalian adenosine receptors or polypeptides. In this invention, amino acid sequence homology, or sequence identity is determined by optimizing residue matches and, if necessary, by introducing gaps as required. Homologous amino acid sequences are typically intended to include natural allelic, polymorphic and interspecies variations in each respective sequence.

Typical homologous proteins or peptides will have from 25–100% homology (if gaps can be introduced) to 50–100% homology (if conservative substitutions are included), with the amino acid sequence of the adenosine receptors. Primate species receptors are of particular interest.

Observed homologies will typically be at least about 35%, preferably at least about 50%, more preferably at least about 75%, and most preferably at least about 80% or more. See Needleham et al., *J. Mol. Biol.* 48:443–453 (1970); Sankoff et al. in *Time Warps, String Edits, and Macromolecules: The Theory and Practice of Sequence Comparison,* 1983, Addison-Wesley, Reading, Mass.; and software packages from IntelliGenetics, Mountain View, Calif., and the University of Wisconsin Genetics Computer Group, Madison, Wis.

Glycosylation variants include, e.g., analogs made by modifying glycosylation patterns during synthesis and processing in various alternative eukaryotic host expression systems, or during further processing steps. Particularly preferred methods for producing glycosylation modifications include exposing the mammalian adenosine receptors to glycosylating enzymes derived from cells that normally carry out such processing, such as mammalian glycosylation enzymes. Alternatively, deglycosylation enzymes can be used to remove carbohydrates attached during production in eukaryotic expression systems. "Homologous nucleic acid sequences" are those which when aligned and compared exhibit significant similarities. Standards for homology in nucleic acids are either measures for homology generally used in the art by sequence comparison or based upon hybridization conditions, which are described in greater detail below.

Substantial nucleotide sequence homology is observed when there is identity in nucleotide residues in two sequences (or in their complementary strands) when optimally aligned to account for nucleotide insertions or deletions, in at least about 50%, preferably in at least about 75%, more preferably in at least about 90%, and most preferably in at least about 95% of the aligned nucleotides.

Substantial homology also exists when one sequence will hybridize under selective hybridization conditions to another. Typically, selective hybridization will occur when there is at least about 55% homology over a stretch of at least about 30 nucleotides, preferably at least about 65% over a stretch of at least about 25 nucleotides, more preferably at least about 75%, and most preferably at least about 90% over about 20 nucleotides. See, e.g., Kanehisa, *Nucleic Acids Res.* 12:203 (1984).

The lengths of such homology comparisons may encompass longer stretches and in certain embodiments may cover a sequence of at least about 17, preferably at least about 25, more preferably at least about 50, and most preferably at least about 75 nucleotide residues.

Stringency of conditions employed in hybridizations to establish homology are dependent upon factors such as salt concentration, temperature, the presence of organic solvents, and other parameters. Stringent temperature conditions usually include temperatures in excess of about 30° C., often in excess of about 37° C., typically in excess of about 45° C., preferably in excess of about 55° C., more preferably in excess of about 65° C., and most preferably in excess of about 70° C. Stringent salt conditions will ordinarily be less than about 1000 mM, usually less than about 500 mM, more usually less than about 400 mM, preferably less than about 300 mM, more preferably less than about 200 mM, and most preferably less than about 150 mM. For example, salt concentrations of 100, 50 and 20 mM are used. The combination of the foregoing parameters, however, is more important than the measure of any single parameter. See, e.g., Wetmur et al., *J. Mol. Biol.* 31:349 (1968).

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The term "substantially pure" is defined herein to mean a mammalian adenosine receptor, nucleic acid or other material that is free from other contaminating proteins, nucleic acids, and other biologicals derived from an original source organism or recombinant DNA expression system. Purity may be assayed by standard methods and will typically exceed at least about 50%, preferably at least about 75%, more preferably at least about 90%, and most preferably at least about 95% purity. Purity evaluation may be made on a mass or molar basis.

Nucleic acids encoding the adenosine receptors or fragments thereof can be prepared by standard methods. For example, DNA can be chemically synthesized using, e.g., the phosphoramidite solid support method of Matteucci et al. [*J. Am. Chem. Soc.* 103:3185 (1981)], the method of Yoo et al. [*J. Biol. Chem.* 764:17078 (1989)], or other well known methods. This can be done by sequentially linking a series of oligonucleotide cassettes comprising pairs of synthetic oligonucleotides, as described below.

Of course, due to the degeneracy of the genetic code, many different nucleotide sequences can encode the adenosine receptors. The codons can be selected for optimal expression in prokaryotic or eukaryotic systems. Such degenerate variants are of course also encompassed by this invention.

Moreover, nucleic acids encoding the adenosine receptors can readily be modified by nucleotide substitutions, nucleotide deletions, nucleotide insertions, and inversions of nucleotide stretches. Such modifications result in novel DNA sequences that encode antigens having immunogenic or antigenic activity in common with the wild-type receptors. These modified sequences can be used to produce wild type or mutant receptors, or to enhance expression in a recombinant DNA system.

Insertion of the DNAs encoding the adenosine receptors into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, desired sites may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., *Science* 239:487 (1988). The cleaved vector and the DNA fragments may also be modified if required by homopolymeric tailing.

Recombinant expression vectors used in this invention are typically self-replicating DNA or RNA constructs comprising nucleic acids encoding one of the mammalian adenosine receptors, usually operably linked to suitable genetic control elements that are capable of regulating expression of the nucleic acids in compatible host cells. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also may contain an origin of replication that allows the vector to replicate independently of the host cell.

Vectors that could be used in this invention include microbial plasmids, viruses, bacteriophage, integratable DNA fragments, and other vehicles that may facilitate integration of the nucleic acids into the genome of the host. Plasmids are the most commonly used form of vector but all other forms of vectors which serve an equivalent function and which are, or become, known in the art are suitable for use herein. See, e.g., Pouwels et al., *Cloning Vectors: A Laboratory Manual*, 1985 and Supplements, Elsevier, N.Y., and Rodriguez et al. (eds.), *Vectors: A Survey of Molecular Cloning Vectors and Their Uses*, 1988, Buttersworth, Boston, Mass.

Expression of nucleic acids encoding the adenosine receptors of this invention can be carried out by conventional methods in either prokaryotic or eukaryotic cells. Although strains of *E. coli* are employed most frequently in prokaryotic systems, many other bacteria such as various strains of *Pseudomonas* and *Bacillus* are know in the art and can be used as well.

Prokaryotic expression control sequences typically used include promoters, including those derived from the β-lactamase and lactose promoter systems [Chang et al., *Nature*, 198:1056 (1977)], the tryptophan (trp) promoter system [Goeddel et al., *Nucleic Acids Res.* 8:4057 (1980)], the lambda $P_L$ promoter system [Shimatake et al., *Nature*, 292: 128 (1981)] and the tac promoter [De Boer et al., *Proc. Natl. Acad. Sci. USA* 292:128 (1983)]. Numerous expression vectors containing such control sequences are known in the art and available commercially.

Suitable host cells for expressing nucleic acids encoding the mammalian adenosine receptors include prokaryotes and higher eukaryotes. Prokaryotes include both gram negative and positive organisms, e.g., *E. coli* and *B. subtilis*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the mammalian adenosine receptors include but are not limited to those containing the lac promoter (pUC-series); trp promoter (pBR322-trp); Ipp promoter (the pIN-series); lambda-pP or pR promoters (pOTS); or hybrid promoters such as ptac (pDR540). See Brosius et al., "Expression Vectors Employing Lambda-, trp-, lac-, and Ipp-derived Promoters", in Rodriguez and Denhardt (eds.) *Vectors: A Survey of Molecular Cloning Vectors and Their Uses*, 1988, Buttersworth, Boston, pp. 205–236.

Higher eukaryotic tissue culture cells are preferred hosts for the recombinant production of the mammalian adenosine receptors. Although any higher eukaryotic tissue culture cell line might be used, including insect baculovirus expression systems, mammalian cells are preferred. Transformation or transfection and propagation of such cells have become a routine procedure. Examples of useful cell lines include HeLa cells, Chinese hamster ovary (CHO) cell lines, baby rat kidney (BRK) cell lines, 293 cell lines, insect cell lines, bird cell lines, and monkey (COS) cell lines.

Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Representative examples of suitable expression vectors include pCR®3.1, pCDNA1, pCD [Okayama et al., *Mol. Cell Biol* 5:1136 (1985)], pMC1neo Poly-A [Thomas et al., *Cell* 51:503 (1987)], pUC19, pREP8, pSVSPORT, pME18s and derivatives thereof, and baculovirus vectors such as pAC 373 or pAC 610.

Protein Purification

The proteins, polypeptides and antigenic fragments of this invention can be purified by standard methods, including but not limited to salt or alcohol precipitation, preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in *Guide to Protein Purification, Methods in Enzymology*, Vol. 182, M. Deutscher, Ed., 1990, Academic Press, New York, N.Y. More specific methods applicable to purification of the adenosine receptors are described below.

Purification steps can be followed by carrying out assays for ligand binding activity as described below. Particularly where a receptor is being isolated from a cellular or tissue source, it is preferable to include one or more inhibitors of proteolytic enzymes is the assay system, such as phenylmethanesulfonyl fluoride (PMSF).

Screening Systems and Methods

The invention allows the discovery of selective agonists and antagonists of the receptor that may be useful in treatment and management of a variety of medical conditions including vasodilation, hypotension, reversal of tachycardia, chronic renal diseases, thyroid disorders, and inflammation including asthma. Thus, the adenosine receptor of this invention can be employed in screening systems to identify agonists or antagonists of the receptor. Essentially, these systems provide methods for bringing together a mammalian adenosine receptor, an appropriate known ligand, including adenosine itself or analogs or surrogates of adenosine, and a sample to be tested for the presence of an adenosine agonist or antagonist.

Two basic types of screening systems can be used, a labeled-ligand binding assay and a "functional" assay. A labeled ligand for use in the binding assay can be obtained by labeling adenosine or a known adenosine agonist or antagonist with a measurable group as described above in connection with the labeling of antibodies. Various labeled forms of adenosine or adenosine surrogates or analogs are available commercially or can be generated using standard techniques. Examples include $^3$H-adenosine, $^3$H-NECA (5'-N-Ethy-carboxamido-adenosine), and $^3$H-R-PIA (R(−)-N6-(2-phenylisopropyl)adenosine).

Typically, a given amount of the adenosine receptor of the invention is contacted with increasing amounts of a labeled ligand, such as labeled adenosine itself or adenosine analogs or surrogates, and the amount of the bound labeled ligand is measured after removing unbound labeled ligand by washing. As the amount of the labeled ligand is increased, a point is eventually reached at which all receptor binding sites are occupied or saturated. Specific receptor binding of the labeled ligand is abolished by a large excess of unlabeled ligand.

Preferably, an assay system is used in which non-specific binding of the labeled ligand to the receptor is minimal. Non-specific binding is typically less than 50%, preferably less than 15%, and more preferably less than 10% of the total binding of the labeled ligand.

As used herein, the term "adenosine ligand" is defined to mean adenosine itself or an analog or surrogate of adenosine. For regulatory purposes it may be desirable to use adenosine or an active fragment thereof as the adenosine ligand in conjunction with the human receptor when screening for adenosine agonists or antagonists for human therapeutic purposes.

In principle, a binding assay of the invention could be carried out using a soluble receptor of the invention, e.g., following production and refolding by standard methods from an *E. coli* expression system, and the resulting receptor-labeled ligand complex could be precipitated, e.g., using an antibody against the receptor. The precipitate could then be washed and the amount of the bound labeled ligand could be measured.

Preferably, however, a nucleic acid encoding one of the adenosine receptors of the invention is transfected into an appropriate host cell, whereby the receptor will become incorporated into the membrane of the cell. A membrane fraction can then be isolated from the cell and used as a source of the receptor for assay. Preferably, specific binding of the labeled ligand to a membrane fraction from the untransfected host cell will be negligible.

The binding assays of this invention can be used to identify both adenosine agonists and antagonists, because both will interfere with the binding of the labeled ligand to the receptor.

In the basic binding assay, the method for identifying a adenosine agonist or antagonist comprises:

(a) contacting a mammalian adenosine receptor having an amino acid sequence defined by SEQ ID NO: 2 or a subsequence thereof, in the presence of a known amount of labeled adenosine or surrogate thereof with a sample to be tested for the presence of an adenosine agonist or antagonist; and (b) measuring the amount of labeled adenosine or surrogate bound to the receptor;

whereby a adenosine agonist or antagonist in the sample is identified by measuring substantially reduced binding of the labeled adenosine or surrogate to the adenosine receptor, compared to what would be measured in the absence of such agonist or antagonist.

Preferably, the adenosine receptor used to identify a adenosine agonist or antagonist for human therapeutic purposes has an amino acid sequence defined by SEQ ID NO: 2 or a subsequence thereof.

In one embodiment of the invention, the foregoing method further comprises:

(c) Contacting a mammalian adenosine receptor in the presence of a known amount of labeled adenosine or surrogate thereof with a compound identified as a adenosine agonist or antagonist in steps (a) and (b); and (d) Measuring the amount of labeled adenosine or surrogate bound to the receptor;

whereby an adenosine agonist or antagonist specific for the adenosine receptor is identified by measuring substantially undiminished binding of the labeled adenosine or surrogate to the receptor, compared to what would be measured in the absence of such agonist or antagonist.

Determination of whether a particular molecule inhibiting binding of the labeled ligand to the receptor is an antagonist or an agonist is then determined in a second, functional assay. The functionality of adenosine agonists and antagonists identified in the binding assay can be determined in cellular and animal models.

Functional Assays for Antagonists/Agonists of Adenosine Receptors

In cellular models, parameters for intracellular activities mediated by adenosine receptors can be monitored for antagonistic and/or agonistic activities. Such parameters include but are not limited to intracellular second messenger pathways activated via the adenosine receptors, changes in cell growth rate, secretion of hormones, etc., using published methods. Examples of such methods are, measurement of the effects of the ligands on receptor-mediated inhibition of forskolin-stimulated intracellular cAMP production [Parker et al., *Mol Brain Res.* 34:179–189 (1995)], receptor-stimulated $Ca^{2++}$ mobilization and mitogenic effects [Sethi et al., *Cancer Res.* 51:1674–1679 (1991)], and inositol phosphate production and MAP kinase induction (Wang et al., *Biochemistry* 37:6711–17 (1998). The FLIPR method described in this invention is also suitable for measuring intracellular release of calcium.

Agonists of adenosine receptors may also be identified directly by using functional assays. An agonist may or may not directly inhibit adenosine binding to adenosine receptors.

In addition to the methods described above, activities of an antagonist may be measured in cellular models for altered intracellular cAMP or $Ca^{2+}$ concentrations. Adenosine-induced chemotaxis using cultured cells can also be utilized. Furthermore, models employing *Xenopus laevis*, pigment dispersion/aggregation in melanophores, and aequorin assay in mammalian cells are suitable for this purpose. Methods using animals or animal tissues for such activities can also be employed. Adenosine-stimulated leukocyte chemotaxis, enhanced leukocyte-endothelial interaction, leukocyte activation leading to changes in the rate of proliferation, degranulation and release of mediators, enzymes and superoxides, inflammatory pain, and increased or decreased cytokine production and transcription are examples of such methods.

Other Mammalian Adenosine Receptors

The present invention provides methods for cloning mammalian adenosine receptors from other mammalian species. Briefly, Southern and Northern blot analysis can be carried out to identify cells from other species expressing genes encoding the adenosine receptors. Complementary DNA (cDNA) libraries can be prepared by standard methods from mRNA isolated from such cells, and degenerate probes or PCR primers based on the nucleic acid and amino acid sequences provided herein can be used to identify clones encoding a adenosine receptor.

Alternatively, expression cloning methodology can be used to identify particular clones encoding a adenosine receptor. An antibody preparation which exhibits cross-reactivity with adenosine receptors from a number of mammalian species may be useful in monitoring expression cloning.

However identified, clones encoding adenosine receptors from various mammalian species can be isolated and sequenced, and the coding regions can be excised and inserted into an appropriate vector.

Other Related Genes

The present invention also provides compositions and methods for cloning other genes related to the gene encoding a polypeptide defined by SEQ ID NO: 2. Specifically, this invention provides a recombinant nucleic acid comprising a sequence having at least about 70% identity over a stretch of at least about 30 nucleotides to the nucleic acid sequence of SEQ ID NO: 1, useful, e.g., as a probe or PCR primer for a related gene.

Localization of mRNA encoding the polypeptide of
SEQ ID NO: 2

The present invention also provides compositions and methods for localization of messenger RNA coding for the polypeptide defined by the amino acid sequence of SEQ ID NO: 2.

Specifically, human multiple tissue and cancer cell line blots containing approximately 2µg of poly(A)+RNA per lane, are purchased from Clontech (Palo Alto, Calif.). Probes are radiolabeled with [$\alpha^{32}$P] dATP, e.g., using the Amersham Rediprime random primer labeling kit (RPN1633). Prehybridization and hybridizations are performed at 65° C. in 0.5M Na$_2$HPO$_4$, 7% SDS, 0.5M EDTA pH 8.0). High stringency washes are conducted, e.g., at 65° C. with two initial washes in 2× SSC, 0.1% SDS for 40 min followed by a subsequent wash in 0.1×SSC, 0.1% SDS for 20min. Membranes are then exposed at −70° C. to X-Ray film (Kodak) in the presence of intensifying screens. More detailed studies by cDNA library Southerns are performed with selected clones of nucleic acids having the nucleotide sequence defined by SEQ ID NO: 1 to examine their expression in other cell subsets.

Two prediction algorithms that take advantage of the patterns of conservation and variation in multiply aligned sequences, (Rost and Sander (1994) *Proteins* 19:5 5–72) and DSC (King and Sternberg (1996) *Protein Sci.* 5:2298–2310), are used.

Alternatively, two appropriate primers are selected and RT-PCR is used on an appropriate mRNA sample selected for the presence of message to produce a cDNA, e.g., a sample which expresses the gene.

Full length clones may be isolated by hybridization of cDNA libraries from appropriate tissues pre-selected by PCR signal.

Message for genes encoding a polypeptide having the amino acid sequence of SEQ ID NO: 2 are assayed by appropriate technology, e.g., PCR, immunoassay, hybridization, or otherwise. Tissue and organ cDNA preparations are available, e.g., from Clontech, Mountain View, Calif.

Southern Analysis on cDNA libraries are performed as follows: DNA (5 µg) from a primary amplified cDNA library is digested with appropriate restriction enzymes to release the inserts, run on a 1% agarose gel and transferred to a nylon membrane (Schleicher and Schuell, Keene, N.H.).

Samples from cDNA libraries from human mRNA isolation may include: peripheral blood mononuclear cells (monocytes, T cells, NK cells, granulocytes, B cells), resting (T100); peripheral blood mononuclear cells, activated with anti-CD3 for 2, 6, 12 h pooled (T101); T cell, TH0 clone Mot 72, resting (T102); T cell, TH0 clone Mot72, activated with anti-CD28 and anti-CD3 for 3, 6, 12 h pooled (T103); T cell,TH0 clone Mot 72, anergic treated with specific peptide for 2, 7, 12 h pooled (T104); T cell, TH1 clone HY06, resting (T107); T cell, TH1 clone HY06, activated with anti-CD28 and anti-CD3 for 3, 6, 12 h pooled (T108); T cell, TH1 clone HY06, anergic treated with specific peptide for 2, 6, 12 h pooled (T109); T cell, TH2 clone HY935, resting (T110); T cell, TH2 clone HY935, activated with anti-CD28 and anti-CD3 for 2, 7, 12 h pooled (T111); T cell, TH2 clone B21, resting (T114); T cell, TH2 B21 activated with anti-CD3 for 5h (T115); T cell, random gamma delta T cell clones, resting (T119); T cell, Jurkat, resting (T120); T cell, Jurkat, activated with PMA and ionomycin for 1, 6 hr pooled (T122); T cell line, CD28-, nonactivated (T123); T cell, TR-1 regulatory cell line (T124); splenocytes, resting (B100); splenocytes, activated with anti-CD40 and IL-4 (B101); B cell EBV lines pooled WT49, RSB, JY, CVIR, 721.221, RM3, HSY, resting (B102); B cell line JY, activated with PMA and ionomycin for 1, 6 h pooled (B103); natural killer (NK) 20 clones pooled, resting (K100); NK 20 clones pooled, activated with PMA and ionomycin for 6 h (K101); NK clone, NKA6, activated with PMA and ionomycin for 6 h (K102); NKL clone, derived from peripheral blood of LGL leukemia patient, IL-2 treated (K106); NK cytotoxic clone 640-A30-1, resting (K107); NK clone, noncytotoxic variant of clone 640-A230-1, resting (K108); hematopoietic precursor line TF1, activated with PMA and ionomycin for 1, 6 h pooled (C100); U937 premonocytic line, resting (M100); U937 premonocytic line, activated with PMA and ionomycin for 1, 6 h pooled (M101); elutriated monocytes, activated with LPS, IFN-γ, anti-IL-10 for 1, 2, 6, 12, 24 h pooled (M102); elutriated monocytes, activated with LPS, IFN-γ, IL-10 for 1, 2, 6, 12, 24 h pooled (M103); elutriated monocytes, activated with LPS, IFN-γ, anti-IL-10 for 4, 16 h pooled (M106); elutriated monocytes, activated with LPS, IFN-γ, IL-10 for 4, 16 h pooled (M107); elutriated monocytes, activated LPS for 1 h (M108); elutriated monocytes, activated LPS for 6 h (M109); primary mast cells (C114); dendritic cells (DC) 70% CD1a+, from CD34+ GM-CSF, TNF-α 12 days, resting (D101); DC 70% CD1a+, from CD34+ GM-CSF, TNF-α 12 days, activated with PMA and ionomycin for 1 hr (D102); DC 70% CD1a+, from CD34+ GM-CSF, TNF-α 12 days, activated with PMA and ionomycin for 6 hr (D103); DC 95% CD1a+, from CD34+ GM-CSF, TNF-α 12 days FACS sorted, activated with PMA and ionomycin for 1, 6 h pooled (D104); DC 95% CD14+, from CD34+ GM-CSF, TNF-α 12 days FACS sorted, activated with PMA and ionomycin 1, 6 hr pooled (D105); DC CD1a+ CD86+, from CD34+ GM-CSF, TNF-α 12 days FACS sorted, activated with PMA and ionomycin for 1, 6 h pooled (D106); DC from monocytes after 5 days in GM-CSF, IL-4, resting (D108); DC from monocytes after 5 days in GM-CSF, IL-4, activated LPS 4, 16 h pooled (D109); DC from monocytes after 5 days in GM-CSF, IL-4, activated TNF-α, monocyte supernatant for 4, 16 h pooled (D110); DC from monocytes after 7 days in GM-CSF, IL-4, resting (D111); DC from monocytes after 7 days in GM-CSF, IL-4, activated by CD40L (D112); DC from CD34+ stem cells after 12 days in GM-CSF, TNF-α and TGF-β, resting (D113); DC from CD34+ stem cells after 12 days in GM-CSF, TNF-α and TGF-β, activated with TNF-α/TGF-β (D114); lung fibroblast sarcoma line MRC5, activated with PMA and ionomycin for 1, 6 h pooled (C101); kidney epithelial carcinoma cell line CHA, activated with PMA and ionomycin for 1, 6 h pooled (C102); A549 epithelial cell line, resting (C109); A549 epithelial cell line, activated with IL1-β 2, 6, 24 hr and pooled (C110); kidney fetal 28 wk male (O100); lung fetal 28 wk male (O101); liver fetal 28 wk male (O0102); heart fetal 28 wk male (O103); brain fetal 28 wk male (O104); small intestine fetal 28 wk male (O107); adipose tissue fetal 28 wk male (O108); ovary fetal 25 wk female (O109); uterus fetal 25 wk female (O110); testes fetal 28 wk male (O111); spleen fetal 28 wk male (O112); adult placenta 28 wk (O113); and tonsil inflamed, from 12 year old (X100); total lung, asthmatic (X114, X117); colon, Crohn's patient (X113, X115, X116).

Antibody Production

Antigenic (i.e., immunogenic) fragments of the mammalian adenosine receptors of this invention, which may or may not have ligand binding activity, may be produced. Regardless of whether they bind adenosine, such fragments, like the complete receptors, are useful as antigens for preparing antibodies by standard methods that can bind to the complete receptors. Shorter fragments can be concatenated or attached to a carrier. Because it is well known in the art that epitopes generally contain at least about five, preferably at least about 8, amino acid residues [Ohno et al., *Proc. Natl. Acad. Sci. USA* 82:2945 (1985)], fragments used for the production of antibodies will generally be at least that size. Preferably, they will contain even more residues, as described above. Whether a given fragment is immunogenic can readily be determined by routine experimentation.

Although it is generally not necessary when complete mammalian adenosine receptors are used as antigens to elicit antibody production in an immunologically competent host, smaller antigenic fragments are preferably first rendered more immunogenic by cross-linking or concatenation, or by coupling to an immunogenic carrier molecule (i.e., a macromolecule having the property of independently eliciting an immunological response in a host animal). Cross-linking or conjugation to a carrier molecule may be required because small polypeptide fragments sometimes act as haptens (molecules which are capable of specifically binding to an antibody but incapable of eliciting antibody production, i.e., they are not immunogenic). Conjugation of such fragments to an immunogenic carrier molecule renders them more immunogenic through what is commonly known as the "carrier effect".

Suitable carrier molecules include, e.g., proteins and natural or synthetic polymeric compounds such as polypeptides, polysaccharides, lipopolysaccharides etc. Protein carrier molecules are especially preferred, including but not limited to keyhole limpet hemocyanin and mammalian serum proteins such as human or bovine gammaglobulin, human, bovine or rabbit serum albumin, or methylated or other derivatives of such proteins. Other protein carriers will be apparent to those skilled in the art. Preferably, but not necessarily, the protein carrier will be foreign to the host animal in which antibodies against the fragments are to be elicited.

Covalent coupling to the carrier molecule can be achieved using methods well known in the art, the exact choice of which will be dictated by the nature of the carrier molecule used. When the immunogenic carrier molecule is a protein, the fragments of the invention can be coupled, e.g., using water-soluble carbodiimides such as dicyclohexylcarbodiimide or glutaraldehyde.

Coupling agents such as these can also be used to cross-link the fragments to themselves without the use of a separate carrier molecule. Such cross-linking into aggregates can also increase immunogenicity. Immunogenicity can also be increased by the use of known adjuvants, alone or in combination with coupling or aggregation.

Suitable adjuvants for the vaccination of animals include but are not limited to Adjuvant 65 (containing peanut oil, mannide monooleate and aluminum monostearate); Freund's complete or incomplete adjuvant; mineral gels such as aluminum hydroxide, aluminum phosphate and alum; surfactants such as hexadecylamine, octadecylamine, lysolecithin, dimethyldioctadecylammonium bromide, N,N-diocta-decyl-N',N'-bis(2-hydroxymethyl) propanediamine, methoxyhexadecylglycerol and pluronic polyols; polyanions such as pyran, dextran sulfate, poly IC, polyacrylic acid and carbopol; peptides such as muramyl dipeptide, dimethylglycine and tuftsin; and oil emulsions. The polypeptides could also be administered following incorporation into liposomes or other microcarriers.

Information concerning adjuvants and various aspects of immunoassays are disclosed, e.g., in the series by P. Tijssen, *Practice and Theory of Enzyme Immunoassays,* 3rd Edition, 1987, Elsevier, N.Y. Other useful references covering methods for preparing polyclonal antisera include *Microbiology,* 1969, Hoeber Medical Division, Harper and Row; Landsteiner, *Specificity of Serological Reactions,* 1962, Dover Publications, New York, and Williams, et al., *Methods in Immunology and Immunochemistry,* Vol. 1, 1967, Academic Press, New York.

Serum produced from animals immunized using standard methods can be used directly, or the IgG fraction can be separated from the serum using standard methods such as plasmaphoresis or adsorption chromatography with IgG-specific adsorbents such as immobilized Protein A. Alternatively, monoclonal antibodies can be prepared.

Hybridomas producing monoclonal antibodies against the adenosine receptors of the invention or antigenic fragments thereof are produced by well-known techniques. Usually, the process involves the fusion of an immortalizing cell line with a B-lymphocyte that produces the desired antibody. Alternatively, non-fusion techniques for generating immortal antibody-producing cell lines can be used, e.g., virally-induced transformation [Casali et al., *Science* 234:476 (1986)]. Immortalizing cell lines are usually transformed mammalian cells, particularly myeloma cells of rodent, bovine, and human origin. Most frequently, rat or mouse myeloma cell lines are employed as a matter of convenience and availability.

Techniques for obtaining antibody-producing lymphocytes from mammals injected with antigens are well known. Generally, peripheral blood lymphocytes (PBLs) are used if cells of human origin are employed, or spleen or lymph node cells are used from non-human mammalian sources. A host animal is injected with repeated dosages of the purified antigen (human cells are sensitized in vitro), and the animal is permitted to generate the desired antibody-producing cells before they are harvested for fusion with the immortalizing cell line. Techniques for fusion are also well known in the art, and in general involve mixing the cells with a fusing agent, such as polyethylene glycol.

Hybridomas are selected by standard procedures, such as HAT (hypoxanthine-aminopterin-thymidine) selection. Those secreting the desired antibody are selected using standard immunoassays, such as Western blotting, ELISA (enzyme-linked immunosorbent assay), RIA (radioimmunoassay), or the like. Antibodies are recovered from the medium using standard protein purification techniques [Tijssen, *Practice and Theory of Enzyme Immunoassays* (Elsevier, Amsterdam, 1985)].

Many references are available to provide guidance in applying the above techniques [Kohler et al., *Hybridoma Techniques* (Cold Spring Harbor Laboratory, New York, 1980); Tijssen, *Practice and Theory of Enzyme Immunoassays* (Elsevier, Amsterdam, 1985); Campbell, *Monoclonal Antibody Technology* (Elsevier, Amsterdam, 1984); Hurrell, *Monoclonal Hybridoma Antibodies. Techniques and Applications* (CRC Press, Boca Raton, Fla., 1982)]. Monoclonal antibodies can also be produced using well-known phage library systems. See, e.g., Huse, et al., *Science* 246:1275 (1989); Ward, et al., *Nature,* 341:544 (1989).

Antibodies thus produced, whether polyclonal or monoclonal, can be used, e.g., in an immobilized form bound to a solid support by well known methods, to purify the receptors by immunoaffinity chromatography.

Antibodies against the antigenic fragments can also be used, unlabeled or labeled by standard methods, as the basis for immunoassays of the mammalian adenosine receptors. The particular label used will depend upon the type of immunoassay. Examples of labels that can be used include but are not limited to radiolabels such as $^{32}$P, $^{125}$I, $^{3}$H and $^{14}$C; fluorescent labels such as fluorescein and its derivatives, rhodamine and its derivatives, dansyl and umbelliferone; chemiluminescers such as luciferia and 2,3-dihydrophthalazinediones; and enzymes such as horseradish peroxidase, alkaline phosphatase, lysozyme and glucose-6-phosphate dehydrogenase.

The antibodies can be tagged with such labels by known methods. For example, coupling agents such as aldehydes, carbodiimides, dimaleimide, imidates, succinimides, bisdiazotized benzandine and the like may be used to tag the antibodies with fluorescent, chemiluminescent or enzyme labels. The general methods involved are well known in the art and are described, e.g., in *Immunoassay: A Practical Guide,* 1987, Chan (Ed.), Academic Press, Inc., Orlando, Fla. Such immunoassays could be carried out, for example, on fractions obtained during purification of the receptors.

The antibodies of the present invention can also be used to identify particular cDNA clones expressing the adenosine receptors in expression cloning systems.

Neutralizing antibodies specific for the ligand-binding site of a receptor can also be used as antagonists (inhibitors) to block adenosine binding. Such neutralizing antibodies can readily be identified through routine experimentation, e.g., by using the radioligand binding assay described infra. Antagonism of adenosine activity can be accomplished using complete antibody molecules, or well-known antigen binding fragments such as Fab, Fc, F(ab)$_2$, and Fv fragments.

Definitions of such fragments can be found, e.g., in Klein, *Immunology* (John Wiley, New York, 1982); Parham, Chapter 14, in Weir, ed. *Immunochemistry,* 4th Ed. (Blackwell Scientific Publishers, Oxford, 1986). The use and generation of antibody fragments has also been described, e.g.: Fab fragments [Tijssen, *Practice and Theory of Enzyme Immunoassays* (Elsevier, Amsterdam, 1985)], Fv fragments [Hochman et al., Biochemistry 12:1130 (1973); Sharon et al., Biochemistry 15:1591 (1976); Ehrlich et al., U.S. Pat. No. 4,355,023] and antibody half molecules (Auditore-Hargreaves, U.S. Pat. No. 4,470,925). Methods for making recombinant Fv fragments based on known antibody heavy and light chain variable region sequences have further been described, e.g., by Moore et al. (U.S. Pat. No. 4,642,334) and by Plückthun [*Bio/Technology* 9:545 (1991)]. Alternatively, they can be chemically synthesized by standard methods.

Anti-idiotypic antibodies, both polyclonal and monoclonal, can also be produced using the antibodies elicited against the receptors as antigens. Such antibodies can be useful as they may mimic the receptors.

Pharmaceutical Compositions

The adenosine receptor agonists and antagonists of this invention can be used therapeutically to stimulate or block the activity of adenosine, and thereby to treat any medical condition caused or mediated by adenosine. The dosage regimen involved in a therapeutic application will be determined by the attending physician, considering various factors which may modify the action of the therapeutic substance, e.g., the condition, body weight, sex and diet of the patient, the severity of any infection, time of administration, and other clinical factors.

Typical protocols for the therapeutic administration of such substances are well known in the art. Administration of the compositions of this invention is typically by parenteral, by intraperitoneal, intravenous, subcutaneous, or intramuscular injection, or by infusion or by any other acceptable systemic method. Often, treatment dosages are titrated upward from a low level to optimize safety and efficacy. Generally, daily dosages will fall within a range of about 0.01 to 20 mg protein per kilogram of body weight. Typically, the dosage range will be from about 0.1 to 5 mg per kilogram of body weight.

Dosages will be adjusted to account for the smaller molecular sizes and possibly decreased half-lives (clearance times) following administration. It will be appreciated by those skilled in the art, however, that the adenosine antagonists of the invention encompass neutralizing antibodies or binding fragments thereof in addition to other types of inhibitors, including small organic molecules and inhibitory ligand analogs, which can be identified using the methods of the invention.

An "effective amount" of a composition of the invention is an amount that will ameliorate one or more of the well-known parameters that characterize medical conditions caused or mediated by adenosine.

Although the compositions of this invention could be administered in simple solution, they are more typically used in combination with other materials such as carriers, preferably pharmaceutical carriers. Useful pharmaceutical carriers can be any compatible, non-toxic substances suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g. *Remington's Pharmaceutical Science,* 17th Ed. (Mack Publishing Company, Easton, Pa., 1990). Alternatively, compositions of the invention may be introduced into a patient's body by implantable drug delivery systems [Urquhart et al., *Ann. Rev. Pharmacol. Toxicol.* 24:199 (1984)].

Therapeutic formulations may be administered in many conventional dosage formulation. Formulations typically comprise at least one active ingredient, together with one or more pharmaceutically acceptable carriers. Formulations may include those suitable for oral, rectal, nasal, or parenteral (including subcutaneous, intramuscular, intravenous and intradermal) administration.

The formulations may conveniently be presented in unit dosage form and may be prepared by any methods well known in the art of pharmacy. See, e.g., Gilman et al. (eds.) (1990), *The Pharmacological Bases of Therapeutics,* 8th Ed., Pergamon Press; and *Remington's Pharmaceutical Sciences,* supra, Easton, Penn.; Avis et al. (eds.) (1993) *Pharmaceutical Dosage Forms: Parenteral Medications* Dekker, New York; Lieberman et al. (eds.) (1990) *Pharmaceutical Dosage Forms: Tablets* Dekker, New York; and Lieberman et al. (eds.) (1990), *Pharmaceutical Dosage Forms: Disperse Systems* Dekker, New York.

The present invention also encompasses anti-idiotypic antibodies, both polyclonal and monoclonal, which are produced using the above-described antibodies as antigens. These antibodies are useful because they may mimic the structures of the receptors.

EXAMPLES

The present invention can be illustrated by the following examples. Unless otherwise indicated, percentages given below for solids in solid mixtures, liquids in liquids, and solids in liquids are on a wt/wt, vol/vol and wt/vol basis, respectively. Sterile conditions were generally maintained during cell culture.

Materials and General Methods

Human marathon-ready cDNAs and RACE kit were from Clontech. Oligonucleotides were custom-synthesized by Gibco Life Technologies. 293-EBNA cell line was obtained from Invitrogen. Adenosines and other ligands were purchased from Sigma Chemicals. Radioligands were from NEN.

Standard methods were used, as described, e.g., in Maniatis et al., *Molecular Cloning: A Laboratory Manual*, 1982, Cold Spring Harbor Laboratory, Cold Spring Harbor Press; Sambrook et al., *Molecular Cloning: A Laboratory Manual*, (2d ed.), Vols 1–3, 1989, Cold Spring Harbor Press, NY; Ausubel et al., *Biology*, Greene Publishing Associates, Brooklyn, N.Y.; or Ausubel, et al. (1987 and Supplements), *Current Protocols in Molecular Biology*, Greene/Wiley, New York; Innis et al. (eds.) *PCR Protocols: A Guide to Methods and Applications*, 1990, Academic Press, N.Y.

Example 1

Cloning and Characterization of the Human Adenosine Receptor

The amino acid sequences of known G-protein coupled receptors (GPCRs) were used to conduct a BLAST search of nucleotide databases. The search identified a nucleotide sequence containing a partial open reading frame encoding a putative GPCR, with homology to purinergic receptors. Comparison of the predicted amino acid sequence of this assemblage with known GPCRs revealed the highest homology to the P2Y 11 purinergic receptor. A full length cDNA clone (SEQ ID NO: 1) containing an open reading frame (ORF) was obtained by RACE PCR using standard techniques and was designated SP166.

Specific sense and antisense oligonucleotide primers for amplifying the SP166 ORF were synthesized beginning with the initiating ATG and covering the stop codon. The sequence of the primers were:

```
5' SP166 primer (with a EcoR1 cloning site)-
                                     (SEQ ID NO:3)
CGGAATTCATGCTGGGGATCATGGCATGGAATGCAAC;
and 3' SP166 primer (with a Not1 cloning site)-
                                     (SEQ ID NO:4)
TATGCGGCCGCCCACCACACTGGACTAGTGGATCCTCA.
```

These primers were used for PCR with the previously described cDNA clone. PCR thermal cycling conditions used were: 35 cycles of 95° C., 30 sec.; 62° C., 30 sec.; 68° C., 2 min. A single band at 1.2 kb was detected from this reaction. This band was cloned into the vector pMX-CD8-myc to form the expression construct pMX-CD8-myc-SP166.

Example 2

Ligand Identification and agonist/antagonist screening assay

To generate stable transfectants, full-length expression constructs were made in the murine IL-3 dependent B-cell line, BAF/3. Human SP166 was cloned into the retroviral vector, pMX-CD8-myc with 5' EcoR1 and 3' Not1 sites. This expression vector possessed a myc epitope tag which was attached to the N-terminus of the receptor to allow for the monitoring of cell surface expression using an anti-myc antibody (Pharmingen, San Diego, Calif.). To generate high-titer retroviral stock, the ecotropic packaging line BOSC 23 was used as described (Onishi, et al. 1996). Culture supernatants from these cells, containing viral particles, were used to infect BAF/3 cells. Transfectants underwent selection with 1 mg/ml G418 and were further enriched by fluorescence-activated cell sorting and single cell cloning using anti-myc antibody to the N-terminal myc tag.

For the assay, growth media was removed and replaced with medium containing RPMI, 10% FBS, and 1 mM Fluo3-AM (Sigma) (dissolved in 10% pluronic acid in DMSO). After 1 hr. at 37° C., the cells were washed with Hanks Balanced Salt Solution (HBSS) lacking phenol red and containing 20 mM HEPES, and 0.1 % BSA (wash buffer). 50,000 cells in a volume of 100 ml were added to the plates, and the plates were placed into a Fluorescent Imaging Plate Reader (FLIPR, Molecular Devices) equilibrated to 37° C. In the FLIPR, changes in intracellular [Ca++] levels were measured by excitation of Fluo3 fluorescence at 488 nm while fluorescence output was monitored at 500–560 nm. Fluorescence was monitored once per second for 1 minute, and every 6 seconds for 2 minutes thereafter. After a 10 sec baseline measurement was established, drugs at 3× final concentration ($1\times10^{-4}$M to $1\times10^{-9}$M) were added in a volume of 50 µl while the fluorescence continued to be monitored. Values extracted for data analysis represented the maximal fluorescence value minus the minimal fluorescence value detected following the drug addition. Drug stock solutions were initially dissolved in water (or DMSO) and diluted to 3× final concentration using wash buffer.

Examination of the activity of naturally occurring nucleotides and nucleosides indicated that SP166 was specifically activated by adenosine. Furthermore, this activation by adenosine is specific to SP166 and is not observed in mock transfected cells. Adenosine analogs are also able to activate SP166 with a rank order of potency Adenosine>Nα-methyladenosine >(R) α-methyladenosine>>(S)α-methyladenosine (inactive).

Example 3

Adenosine Binding Assay

Membrane preparation: Cells transfected with SP166 as described above were harvested by incubating in 5 mM EDTA/phosphate-buffered saline followed by repeated pipetting. The cells were centrifuged 5 min at 1000× g. The EDTA/PBS was decanted and an equal volume of ice-cold 50 mM Tris-HCl, pH 7.5, was added and cells were broken up with a Polytron (PT10 tip, setting 5, 30 sec). Nuclei and unbroken cells were sedimented at 1000× g for 10 min and then the supernatant was centrifuged at 50,000× g for 10 min. The supernatant was decanted, the pellet was resuspended by Polytron, a sample was taken for protein assay (bicinchoninic acid, Pierce), and the tissue was again centrifuged at 50,000× g. Pellets were stored frozen at −20° C.

Binding assay: For saturation binding, four concentrations of [$^3$H]-NECA were incubated without and with $10^{-5}$M adenosine in triplicate with 50 µg of membrane protein in a total volume of 200 µl of 50 mM Tris-HCl, pH 7.5, for 30 min at 30° C. Samples were filtered on GF/B filters and washed thrice with 2 ml of cold Tris buffer. Filters were dried in a microwave oven, impregnated with Meltilex wax scintillant, and counted at 45% efficiency. For competition binding assays, five concentrations of compounds were incubated in triplicate with 18 nM [$^3$H]NECA and 70 µg of membrane protein under the conditions described above. Curves were fit to the data with Prism (GraphPad Software) nonlinear least-squares curve-fitting program and Ki values were derived from IC50 values according to Cheng and Prusoff (Cheng, Y. C., and Prusoff, W. H. (1973) Relationship between the inhibition constant (Ki) and the concentration of inhibitor which causes 50 per cent inhibition (IC50) of an enzymatic reaction. *Biochem. Pharmacol.* 22, 3099–3108).

Optimization of the above assay conditions is ongoing.

Example 4 mRNA Cell/Tissue Distribution

Total cellular RNA was isolated from cells by one of two standard methods: 1) guanidine isothiocyanate/Cesium chloride density gradient centrifugation (Maniatis et al., Molecular Cloning: A Laboratory Manual, 1982, Cold Spring Harbor Laboratory, Cold Spring Harbor Press); or with the Tri-Reagent protocol according to the manufacturer's specifications (Molecular Research Center, Inc., Cincinatti, Ohio). Total RNA prepared by the Tri-reagent protocol was treated with DNAse I to remove genomic DNA contamination. For library construction, Poly A+ mRNA was selected using Oligotex kit from Qiagen (Santa Clarita, Calif.) according to the manufacturer's specifications. Libraries were constructed using standard methods (Maniatis et al., Molecular Cloning: A Laboratory Manual, 1982, Cold Spring Harbor Laboratory, Cold Spring Harbor Press).

For relative quantitation of the mRNA distribution of SP166, total RNA from each cell or tissue source was first reverse transcribed. Two µg of total RNA was reverse transcribed using 25 pmole random hexamer primers and 100 pmole poly dT$_{15}$ (Boehringer Mannheim, Indianapolis, Ind.), 0.5 mM each of dATP, dCTP, dGTP and dTTP (Pharmacia, Uppsala, Sweden), 5 mM DTT, 1 µl RNAsin (Promega, Madison Wis.) in a final volume of 20 µl. The first strand synthesis buffer and Superscript II (1 µl/20 µl) reverse transcriptase were from Gibco/BRL (Gaithersburg, Md.). Replicate samples were also prepared similarly with the exception that no Superscript II reverse transcriptase was added; these samples serve as controls for genomic contamination. The reaction was incubated at 42–45° C. for 90 minutes, heated to 95° C. for 5 min and cooled on ice. The volume was adjusted to 200 µl with Tris HCl pH 7.4, yielding a final concentration of 10 ng/µl of starting RNA.

For determination of relative expression of SP166 in various cDNA libraries 5 µg of each library was loaded onto a 2% agarose gel and electrophoresed. The DNA was transferred to a nylon membrane by capillary blotting and then the membrane was probed with a $^{32}$P-labeled cDNA corresponding to the open reading frame region (ORF) of SP166.

Expression was observed in elutriated human monocytes activated with LPS for 1 hour and was increased in monocytes activated with LPS for 6 hours. Expression was also observed in monocytes activated with LPS, interferon gamma and IL-10 for 4 and 16 hours and reduced in the presence of neutralizing antibodies to IL-10. U937 cells expressed high levels of SP166 that was increased with PMA and ionomycin stimulation. B cell lines showed low levels of expression as did fetal spleen, fetal liver, CHA cells, normal thyroid and normal lung.

SP166 expression was also high in monocyte and CD34$^+$ progenitor cell-derived dendritic cells with the exception of those cells activated by LPS. Dendritic cells activated with PMA and Ionomycin, however, do show high levels of SP166 expression.

For dot blot analysis of SP166 commercial membranes (Clontech) were obtained and probed with $^{32}$P-labeled SP166 ORF according to manufacturer's instructions. Kidney and thyroid showed high levels of expression, fetal kidney, fetal liver, fetal spleen, lymph node, bone marrow, spleen and liver showed moderate levels of expression, and heart, aorta, lung and trachea exhibited low levels of expression.

Many modifications and variations of this invention can be made without departing from its spirit and scope, as will be apparent to those skilled in the art. The specific embodiments described herein are offered by way of example only, and the invention is to be limited only by the terms of the appended claims, together with the full scope of equivalents to which such claims are entitled.

What is claimed is:

1. An isolated or recombinant nucleic acid encoding a polypeptide comprising the amino acid sequence of SEQ ID NO: 2.

2. A recombinant vector comprising the nucleic acid of claim 1.

3. A host cell comprising the recombinant vector of claim 2.

4. A method for making a polypeptide comprising the amino acid sequence of SEQ ID NO: 2, comprising culturing the host cell of claim 3 under conditions in which the nucleic acid is expressed.

5. The method of claim 4, further comprising isolating the polypeptide.

6. The host cell of claim 3, wherein the host cell is a prokaryotic cell.

7. The prokaryotic cell of claim 6, wherein the prokaryotic cell is a bacterial cell.

8. The bacterial cell of claim 7, wherein the bacterial cell is from a bacterial strain selected from the group consisting of E. coil, Pseudomonas, and Bacillus.

9. The host cell of claim 3, wherein the host cell is a eukaryotic cell.

10. The eukaryotic cell of claim 9, wherein the eukaryotic cell is a mammalian cell.

11. The mammalian cell of claim 10, wherein the mammalian cell is selected from the group consisting of a HeLa cell, a Chinese hamster ovary (CHO) cell, a baby rat kidney (BRK) cell, a 293 cell, an insect cell, a bird cell, and a COS cell.

12. The recombinant vector of claim 2, wherein the vector is selected from the group consisting of a plasmid, a virus, and a bacteriophage.

13. The recombinant vector of claim 2, wherein the vector is a expression vector.

14. The recombinant vector of claim 13, wherein the nucleic acid is operatively linked to a promoter sequence.

15. The nucleic acid of claim 1, comprising the nucleotide sequence of SEQ ID NO: 1.

16. A recombinant vector comprising the nucleic acid of claim 15.

17. The recombinant vector of claim 16, wherein the vector is selected from the group consisting of a plasmid, a virus, and a bacteriophage.

18. A host cell comprising the recombinant vector of claim 16.

19. The host cell of claim 18, wherein the host cell is a prokaryotic cell.

20. The prokaryotic cell of claim 19, wherein the prokaryotic cell is a bacterial cell.

21. The bacterial cell of claim 20, wherein the bacterial cell is from a bacterial strain selected from the group consisting of E. coil, Pseudomonas, and Bacillus.

22. The host cell of claim 18, wherein the host cell is a eukaryotic cell.

23. The eukar-yotic cell of claim 22, wherein the eukaryotic cell is a mammalian cell.

24. The mammalian cell of claim 23, wherein the mammalian cell is selected from the group consisting of a HeLa cell, a Chinese hamster ovary (CHO) cell, a baby rat kidney (BRK) cell, a 293 cell, an insect cell, a bird cell, and a COS cell.

25. A method for making a polypeptide comprising the amino acid sequence of SEQ ID NO: 2, comprising culturing the host cell of claim 18 under conditions in which the nucleic acid is expressed.

26. The method of claim 25, further comprising isolating the polypeptide.

27. The recombinant vector of claim 16, wherein the vector is a expression vector.

28. The recombinant vector of claim 27, wherein the nucleic acid is operatively linked to a promoter sequence.

* * * * *